(12) United States Patent
Yaoka et al.

(10) Patent No.: US 10,501,922 B2
(45) Date of Patent: Dec. 10, 2019

(54) SANITARY WASHING DEVICE

(71) Applicant: TOTO LTD., Kitakyushu-shi, Fukuoka (JP)

(72) Inventors: Toshinari Yaoka, Kitakyushu (JP); Yoichi Murase, Kitakyushu (JP); Hiroaki Amemori, Kitakyushu (JP)

(73) Assignee: TOTO LTD., Kitakyushu-shi, Fukuoka ( * ) Notice: Subject to any disclaimer, the term of this patent is extended or adjusted under 35 U.S.C. 154(b) by 39 days.

(21) Appl. No.: 15/708,691

(22) Filed: Sep. 19, 2017

(65) Prior Publication Data

US 2018/0002912 A1 Jan. 4, 2018

Related U.S. Application Data

(63) Continuation of application No. PCT/JP2016/053049, filed on Feb. 2, 2016.

(30) Foreign Application Priority Data

Mar. 27, 2015 (JP) ................................ 2015-066630

(51) Int. Cl.
*E03D 9/08* (2006.01)
*A61L 2/26* (2006.01)
(Continued)

(52) U.S. Cl.
CPC .................. *E03D 9/08* (2013.01); *A61L 2/26* (2013.01); *B05B 1/12* (2013.01); *B05B 1/16* (2013.01);
(Continued)

(58) Field of Classification Search
CPC .. E03D 9/08; B05B 15/70; B05B 1/12; A61L 2/10; A51L 2/26; C03F 1/325
(Continued)

(56) References Cited

U.S. PATENT DOCUMENTS 8,978,172 B2 * 3/2015 Plate .......................... E03D 1/01
4/300
2012/0124730 A1 5/2012 Morotomi et al.
(Continued)

FOREIGN PATENT DOCUMENTS

JP 2000-096675 A 4/2000
JP 2001-259622 A 9/2001
(Continued)

OTHER PUBLICATIONS

International Search Report for PCT/JP2016/053049 dated May 10, 2016.

*Primary Examiner* — Huyen D Le
(74) *Attorney, Agent, or Firm* — Pearne & Gordon LLP (57) ABSTRACT

A sanitary washing device including: a nozzle discharging water toward a human body private part; a water guide part including a pipe line reaching from a water supply source to the nozzle, and guiding water supplied from the water supply source to the nozzle; a vacuum breaker provided on a path of the water guide part, and taking air into the pipe line when water does not flow in the water guide part; and an ultraviolet irradiation part provided between the vacuum breaker and the nozzle on the path of the water guide part, and including a flow channel flowing water and a light emitting part irradiating ultraviolet rays to the water flowing in the flow channel is provided.

10 Claims, 7 Drawing Sheets

(51) Int. Cl.
    *B05B 1/16*       (2006.01)
    *B05B 9/00*       (2006.01)
    *B05B 12/00*     (2018.01)
    *B05B 12/12*     (2006.01)
    *C02F 1/32*       (2006.01)
    *B05B 1/12*       (2006.01)
    *B05B 15/70*     (2018.01)
    *A61L 2/10*       (2006.01)
    *C02F 103/42*    (2006.01)

(52) U.S. Cl.
    CPC ............ *B05B 9/002* (2013.01); *B05B 12/008* (2013.01); *B05B 12/122* (2013.01); *B05B 15/70* (2018.02); *C02F 1/325* (2013.01); *A61L 2/10* (2013.01); *A61L 2202/11* (2013.01); *C02F 2103/42* (2013.01); *C02F 2201/3228* (2013.01); *C02F 2303/04* (2013.01); *C02F 2307/06* (2013.01)

(58) Field of Classification Search
    USPC .............................................. 4/443
    See application file for complete search history.

(56) References Cited

U.S. PATENT DOCUMENTS

| | | | |
|---|---|---|---|
| 2013/0036544 A1* | 2/2013 | Lee | A61G 9/003 4/443 |
| 2013/0152295 A1* | 6/2013 | Huang | A47K 3/26 4/443 |
| 2017/0056042 A1* | 3/2017 | Nakagawa | A61B 17/3203 |
| 2017/0067240 A1* | 3/2017 | Komatsu | E03D 9/00 |

FOREIGN PATENT DOCUMENTS

| | | |
|---|---|---|
| JP | 2007-031983 A | 2/2007 |
| JP | 2009-118918 A | 6/2009 |
| JP | 2012-122195 A | 6/2012 |

\* cited by examiner

SANITARY WASHING DEVICE

CROSS-REFERENCE TO RELATED APPLICATIONS

This is a continuation application of International Application PCT/JP2016/053049, filed on Feb. 2, 2016. This application also claims priority to Japanese Application No. 2015-066630, filed on Mar. 27, 2015. The entire contents of each are incorporated herein by reference.

FIELD

An aspect of the invention generally relates to a sanitary washing device, and specifically relates to a sanitary washing device washing "a bottom" or the like of a user sitting down on a western-style sit-down toilet bowl with water.

BACKGROUND

Reduction of bacteria in tap water used for washing water of the sanitary washing device is performed by killing or deactivating bacteria (microorganism) which possibly causes disease or corruption by chlorine. However, only mixture of chlorine does not remove the bacteria contained in the tap water perfectly. Therefore, it is proposed that the bacteria contained in the washing water are reduced by providing an ultraviolet irradiation part for irradiating ultraviolet rays to the washing water on the sanitary washing device (Japanese examined patent publication H05-004499).

The sanitary washing device may be provided with a vacuum breaker on a flow channel for suppressing the water from flowing backward from a nozzle from which the washing water is sprayed toward a body. It is desired for the sanitary washing device including the vacuum breaker that the ultraviolet irradiation part is disposed at an adequate position and safer washing water can be supplied.

DETAILED DESCRIPTION

The first invention is a sanitary washing device comprising: a nozzle discharging water toward a human body private part; a water guide part including a pipe line reaching from a water supply source to the nozzle, and guiding water supplied from the water supply source to the nozzle; a vacuum breaker provided on a path of the water guide part, and taking air into the pipe line when water does not flow in the water guide part; and an ultraviolet irradiation part provided between the vacuum breaker and the nozzle on the path of the water guide part, and including a flow channel flowing water and a light emitting part irradiating ultraviolet rays to the water flowing in the flow channel.

According to this sanitary washing device, even if bacteria is contained in air taken into the vacuum breaker, the bacteria contained in the water can be reduced by the ultraviolet irradiation part disposed on a downstream side of the vacuum breaker. Thereby, safer washing water can be supplied.

The second invention is the sanitary washing device in the first invention, further comprising: a flow channel switching part provided on the path of the water guide part, the nozzle including a plurality of water discharge ports, the flow channel switching part switching a state of communicating with the pipe line and a state of not communicating with the pipe line with respect to each of the plurality of water discharge ports, and the ultraviolet irradiation part being provided between the vacuum breaker and the flow channel switching part.

According to this sanitary washing device, since the ultraviolet irradiation part is provided on an upstream side of the flow channel switching part, even if the washing water is discharged from any water discharge port of the multiple water discharge ports, the bacteria can be reduced. Therefore, one ultraviolet irradiation part can correspond to the multiple water discharge ports.

The third invention is the sanitary washing device in the first invention, wherein the flow channel includes a main part, and a reflection part provided inside the main part and reflecting the ultraviolet rays, and a reflectance of the reflection part to the ultraviolet rays is higher than a reflectance of the main part.

The fourth invention is the sanitary washing device in the second invention, wherein the flow channel includes a main part, and a reflection part provided inside the main part and reflecting the ultraviolet rays, and a reflectance of the reflection part to the ultraviolet rays is higher than a reflectance of the main part.

According to these sanitary washing devices, it is possible to reflect easily the ultraviolet rays in the flow channel. Light absorption on an inner surface of the flow channel can be suppressed. For example, it is possible to make the light reach the details of the flow channel and reduce the bacteria contained in the water effectively.

The fifth invention is the sanitary washing device in the first invention, wherein at least a portion of the flow channel has a straight pipe shape, the light emitting part is a light emitting element, and an irradiation direction of the ultraviolet rays of the light emitting element is the same as an extending direction of at least the portion of the flow channel.

The sixth invention is the sanitary washing device in the second invention, wherein at least a portion of the flow channel has a straight pipe shape, the light emitting part is a light emitting element, and an irradiation direction of the ultraviolet rays of the light emitting element is the same as an extending direction of at least the portion of the flow channel.

According to these sanitary washing devices, it is possible to lengthen the time that the ultraviolet rays are incident on the water, and the bacteria can be reduced more certainly.

The seventh invention is the sanitary washing device in the first invention, wherein the light emitting part is a mercury lamp extending in one direction, and the flow channel is formed in a form being along the one direction of the mercury lamp.

The eighth invention is the sanitary washing device in the second invention, wherein the light emitting part is a mercury lamp extending in one direction, and the flow channel is formed in a form being along the one direction of the mercury lamp.

According to these sanitary washing devices, it is possible to lengthen the time that the ultraviolet rays are incident on the water, and the bacteria can be reduced more certainly.

Embodiments of the invention will now be described with reference to the drawings. Note that the same numerals are applied to similar constituent elements in the drawings and detailed descriptions of such constituent elements are appropriately omitted.

Figure 1:
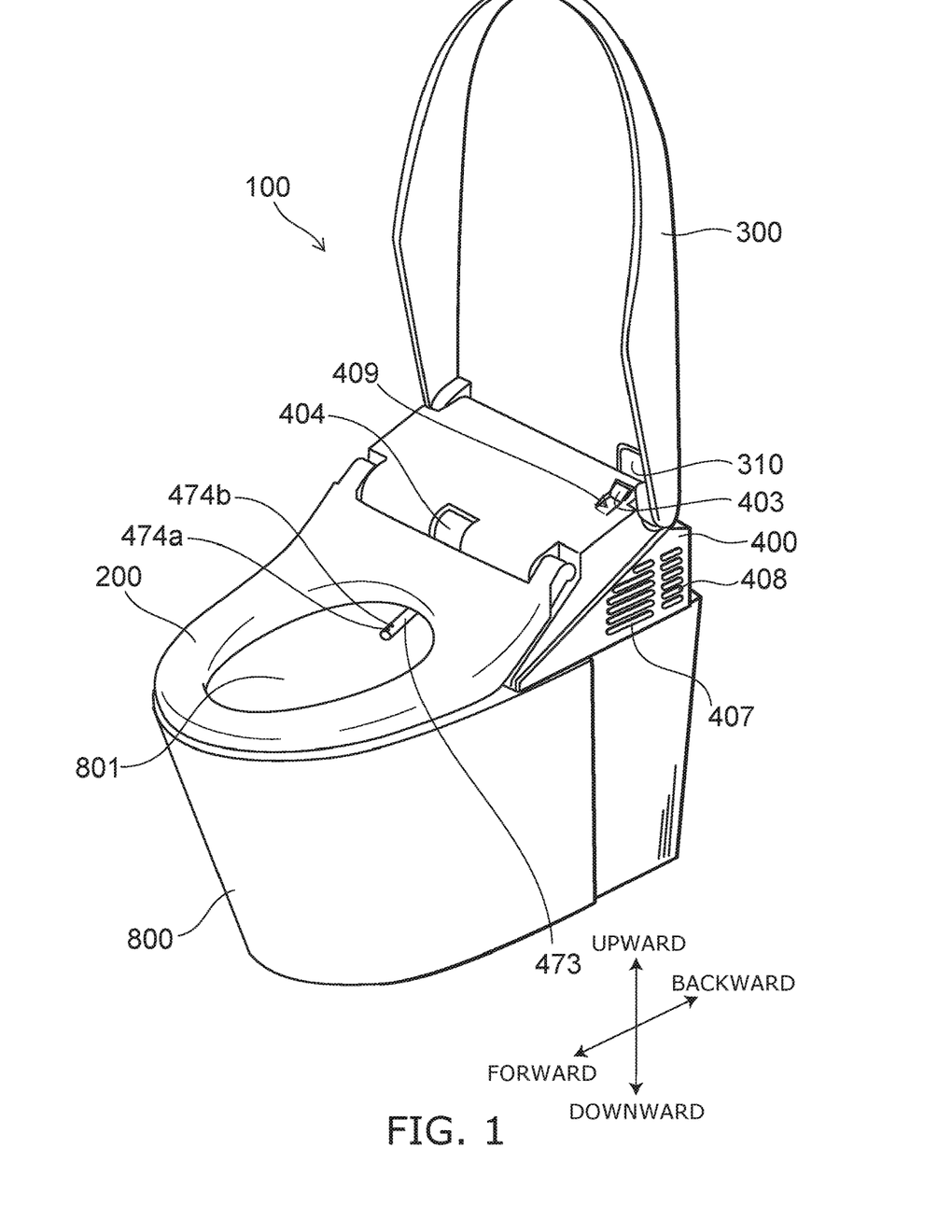
FIG. 1 is a schematic perspective view showing a toilet apparatus including a sanitary washing device according to an embodiment of the invention.

FIG. 1 is a schematic perspective view showing a toilet apparatus including a sanitary washing device according to an embodiment of the invention.

As shown in FIG. 1, the toilet apparatus includes a western-style sit-down toilet bowl (hereinafter, for convenience of the description, simply referred to as "bowl") 800 and a sanitary washing device 100 provided thereon. The sanitary washing device 100 includes a casing 400, a toilet seat 200, and a toilet lid 300. The toilet seat 200 and the toilet lid 300 are pivotally supported freely openable to the casing 400, respectively.

A body washing function part or the like is incorporated inside the casing 400, which realizes washing of the "bottom" or the like of the user sitting on the toilet seat 200. For example, the casing 400 is provided with a seating detection sensor 404 detecting the user sitting on the toilet seat 200. In the case where the seating detection sensor 404 detects the user sitting on the toilet seat 200, when the user operates an operation part adjustment part, for example, such as a remote control, a washing nozzle (hereinafter, for convenience of the description, simply referred to as "nozzle") 473 can be advanced into a bowl 801 of the toilet bowl 800. FIG. 1 shows a state in which the nozzle 473 of the sanitary washing device 100 advances into the bowl 801.

The nozzle 473 discharges water toward a human body private part to wash the human body private part. A bidet washing water discharge port 474a and a bottom washing water discharge port 474b are provided at a distal end portion of the nozzle 473. The nozzle sprays water from the bidet washing water discharge port 474a provided at the distal end and can wash the female private part of the female sitting on the toilet seat 200. Or the nozzle 473 sprays water from the bottom washing water discharge port 474b provided at the distal end and can wash the "bottom" of the user sitting on the toilet seat 200. Note that in the specification of the application "water" is assumed to include not only cold water but also heated hot water.

A mode of washing "bottom" includes, for example, "bottom washing" and "soft washing" washing gently with a water flow softer than "bottom washing". The nozzle 473 can perform, for example, "bidet washing", "bottom washing", and "soft washing".

The nozzle 473 shown in FIG. 1 is provided with the bidet washing water discharge port 474a on a distal end side of the nozzle 473 to the bottom washing water discharge port 474b, locations of the bidet washing water discharge port 474a and the bottom washing water discharge port 474b are not limited thereto. The bidet washing water discharge port 474a may be provided on a rear side of the nozzle 473 to the bottom washing water discharge port 474b. The nozzle 473 shown in FIG. 1 is provided with two water discharge ports, however mat be provided with three or more water discharge ports.

Figure 2:
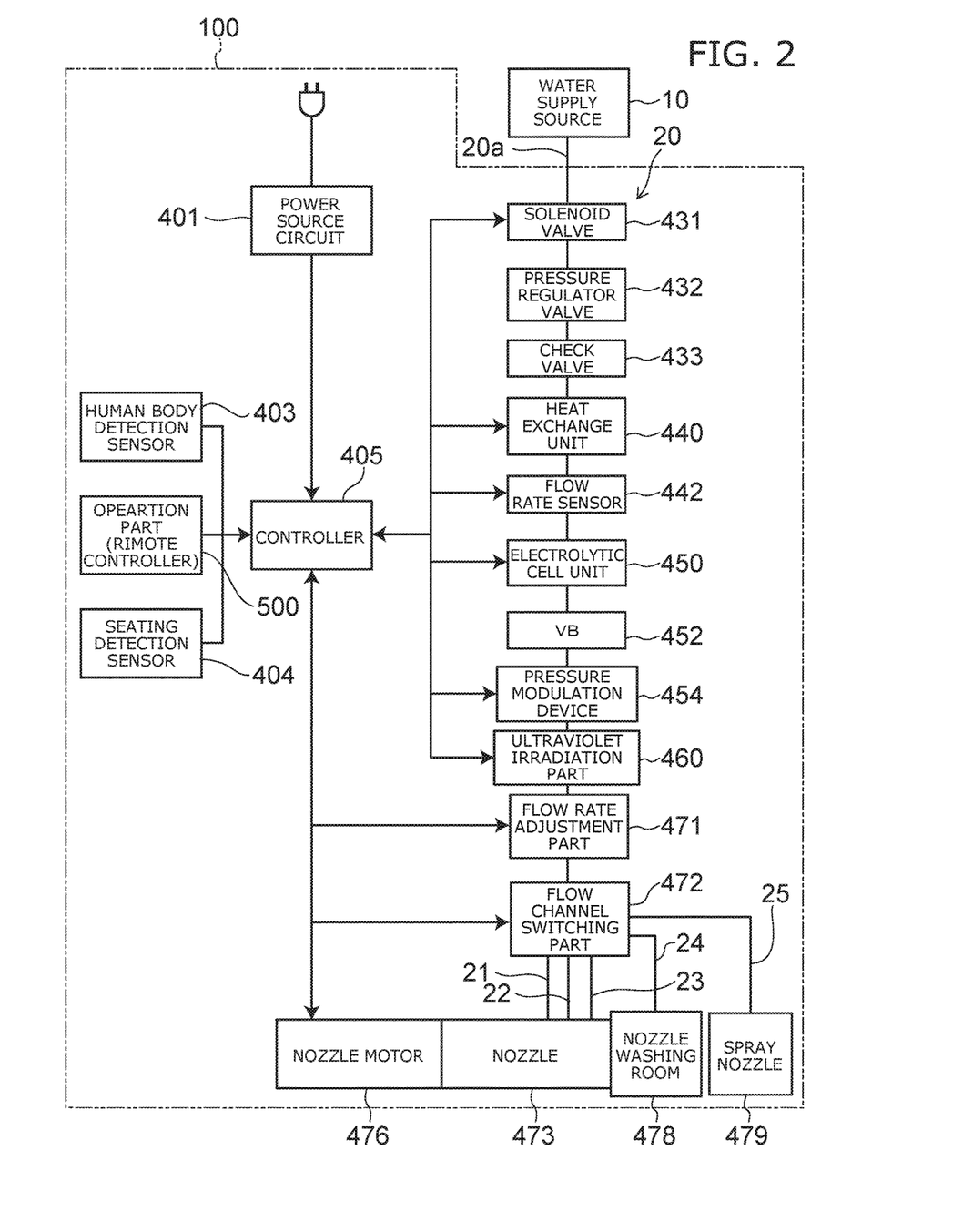
FIG. 2 is a block diagram showing a relevant configuration of the sanitary washing device according to the embodiment.

FIG. 2 is a block diagram showing a relevant configuration of the sanitary washing device according to the embodiment.

FIG. 2 also shows relevant configurations of a water channel system and an electrical system.

As shown in FIG. 2, the sanitary washing device 100 includes a water guide part 20. The water guide part 20 includes a pipe line 20a reaching from a water supply source 10 such as tap water and a water storage tank to the nozzle 473. The pipe line 20 guides the water supplied from the water supply source 10 by through the pipe line 20a to the nozzle 473. The pipe line 20a is formed from, for example, respective parts such as a solenoid valve 431, a heat exchange unit 440, a flow channel switching part 472 described in the following, and multiple pipes connecting these respective parts.

The solenoid valve 431 is provided on an upstream side of the water guide part 20. The solenoid valve 431 is an openable and closable solenoid valve, and controls water supply based on the command from the controller 405 provided inside the casing 400. In other words, the solenoid valve 431 opens/closes the pipe line 20a. By setting the solenoid valve 431 to an open state, the water supplied from the water supply source 10 flows into the pipe line 20a.

A pressure regulator valve 432 is provided on a downstream of the solenoid valve 431. The pressure regulator valve 432 regulates the pressure in the pipe line 20a within a prescribed pressure range when a water supply pressure is high. A check valve 433 is provided on a downstream of the pressure regulator valve 432. The check valve 433 suppresses the backward flow of the water to an upstream side to the check valve 433 when the pressure in the pipe line 20a is lowered.

The heat exchange unit 440 is provided on a downstream of the check valve 433. The heat exchange unit 440 includes a heater and heats the water supplied from the water supply source 10, and the temperature rises to the prescribed temperature. That is, the heat exchange unit 440 generates warm water.

The heat exchange unit 440 of the embodiment is, for example, an instantaneous heating type (instantaneous type) heat exchanger based on a ceramic heater or the like, compared with a warm water heating type heat exchanger based on a warm water storage tank, it is possible to raise the temperature of the water to the prescribed temperature in a short time. The heat exchange unit 440 is not limited to the instantaneous heating type heat exchanger and may be the warm water heating type heat exchanger.

The heat exchange unit 440 is connected to the controller 405. The controller 405 raises the temperature of the water to the temperature set by the operation part 500, for example, by controlling the heat exchange unit 440 in response to the operation of the operation part 500 by the user.

A flow rate sensor 442 is provided on a downstream of the heat exchange unit 440. The flow rate sensor 442 detects the flow rate of the water discharged from the heat exchange unit 440. That is, the flow rate sensor 442 detects the flow rate of the water flowing in the pipe line 20a. The flow rate sensor 442 is connected to the controller 405. The flow rate sensor 442 inputs detection results of the flow rate to the controller 405.

An electrolytic cell unit 450 is provided on a downstream of the flow rate sensor 442. The electrolytic cell unit 450 generates a liquid (functional water) containing hypochlorous acid from tap water by electrolyzing the tap water flowing in the interior. The electrolytic cell unit 450 is connected to the controller 405. The electrolytic cell unit 450 generates the functional water based on the control of the controller 405.

The functional water generated in the electrolytic cell unit 450 may be a solution containing, for example, metal ion such as silver ion or copper ion. The functional water generated in the electrolytic cell unit 450 may be a solution containing electrolytic chlorine or ozone. The functional water generated in the electrolytic cell unit 450 may be acidic water or alkaline water.

A vacuum breaker (VB) 452 is provided on a downstream of the electrolytic cell unit 450. The vacuum breaker 452 includes, for example, a flow channel for flowing water, a suction port for taking air into the flow channel, and a valve mechanism opening/closing the suction port. The valve mechanism, for example, stops the suction port when water is flowing in the flow channel, opens the suction port with stop of the water flow, and takes air into the flow channel. That is, the vacuum breaker 452 takes air into the pipe line 20a when water does not flow in the water guide part 20. A float valve is used for the valve mechanism, for example.

The vacuum breaker 452 promotes water drainage of a portion of the pipe line 20a below the vacuum breaker 452 by taking air into the pipe line 20a as described above. The vacuum breaker 452 promotes, for example, water drainage of the nozzle 473. In this way, the vacuum breaker 452 drains water in the nozzle 473 and takes air into the nozzle 473, and thus, for example, suppresses the washing water in the nozzle 473 and dirty water collected in the bowl 801 from flowing backward to the water supply source 10 (clean water) side.

A pressure modulation device 454 is provided on the downstream of the vacuum breaker 452. The pressure modulation device 454 adds pulsation or acceleration to the water in the pipeline 20a of the water guide part 20, and adds pulsation to the water discharged from the bidet washing water discharge port 474a and the bottom washing water discharge port 474b of the nozzle 473 and a water discharge part of a nozzle washing room 478. That is, the pressure modulation device 454 varies flow state of the water flowing in the pipe line 20a. The pressure modulation device 454 is connected to the controller 405. The pressure modulation device 454 varies the flow state of the water based on the control of the controller 405.

An ultraviolet irradiation part 460 is provided on a downstream of the pressure modulation device 454. The ultraviolet irradiation part 460 irradiates ultraviolet rays to the water flowing in the pipe line 20a. The ultraviolet irradiation part 460, for example, kills or deactivates at least a portion of the bacteria contained in the water flowing in the pipe line 20a by irradiation of ultraviolet rays. Thereby, the ultraviolet irradiation part 460 reduces live bacteria contained in the water flowing in the pipe line 20a. The ultraviolet irradiation part 460, for example, sterilizes washing water by irradiation of ultraviolet rays. The ultraviolet irradiation part 460 is connected to the controller 405. The ultraviolet irradiation part 460 irradiates ultraviolet rays based on control of the controller 405.

A flow rate adjustment part 471 is provided on a downstream of the ultraviolet irradiation part 460. The flow rate adjustment part 471 adjusts water force (flow rate). A flow channel switching part 472 is provided on a downstream of the flow rate adjustment part 471. The flow channel switching part 472 performs opening/closing and switching of water supply to the nozzle 473 and the nozzle washing room 478. The flow rate adjustment part 471 and the flow channel switching part 472 may be provided as one unit. The flow rate adjustment part 471 and the flow channel switching part 472 are connected to the controller 405. The operation of the flow rate adjustment part 471 and the flow channel switching part 472 is controlled by the controller 405.

The nozzle 473, the nozzle washing room 478, and a spray nozzle 479 are provided on a downstream of the flow channel switching part 472. The nozzle 473 receives a driving force from a nozzle motor 476, and advances into the bowl 801 of the toilet bowl 800 and recedes. That is, the nozzle motor 476 advances/retract the nozzle 473 based on the command from the controller 405.

The nozzle washing room 478 washes an outer peripheral surface (trunk) of the nozzle 473 by spraying functional water or water from the water discharge part provided in the interior. The spray nozzle 479 sprays the washing water and the functional water to the bowl 801 in mist form. In this example, the spray nozzle 479 is provided separately from the nozzle for washing the human body. Without limitation to the above, a water discharge port for spraying mist-like liquid to the bowl 801 may be provided in the nozzle 473.

A bottom washing flow channel 21, a soft washing flow channel 22, and a bidet washing flow channel 23 are provided on a downstream of the flow channel switching part 472. The bottom washing flow channel 21 and the soft washing flow channel 22 guide the water supplied from the water supply source 20 via the water guide part 20 and the functional water generated in the electrolytic cell unit 450 to the bottom washing water discharge port 474b. The bidet washing flow channel 23 guides the water supplied from the water supply source 20 via the water guide part 20 and the functional water generated in the electrolytic cell unit 450 to the bidet washing water discharge port 474a.

A surface washing flow channel 24 and a flow channel for spray 25 are provided on a downstream of the flow channel switching part 472. The surface washing flow channel 24 guides the water supplied from the water supply source 20 via the water guide part 20 and the functional water generated in the electrolytic cell unit 450 to the water discharge part of the nozzle washing room 478. The flow channel for spray 25 guides the water supplied from the water supply source 20 via the water guide part 20 and the functional water generated in the electrolytic cell unit 450 to the spray nozzle 479.

The controller 405 switches opening/closing of the respective flow channels of the bottom washing flow channel 21, the soft washing flow channel 22, the bidet washing flow channel 23, the surface washing flow channel 24, and the flow channel for spray 25 by controlling the flow channel switching part 472. In this way, the flow channel switching part 472 switches a state of communicating with the pipe line 20a and a state of not communicating with the pipe line 20a with respect to each of the multiple water discharge ports such as the bidet washing water discharge port 474a, washing water discharge port 474b, the nozzle washing room 478, and the spray nozzle 479.

The controller 405 is supplied with power from a power source circuit 401, and controls operations of the solenoid valve 431, the heat exchange unit 440, the electrolytic cell unit 450, the pressure modulation device 454, the ultraviolet irradiation part 460, the flow rate adjustment part 471, the flow channel switching part 472, the nozzle motor 476 or the like based on signals from a human body detection sensor 403, the seating detection sensor 404, the flow rate sensor 442, the operation part 500 or the like.

The human body detection sensor 403 is provided to be buried in a recessed part 409 formed on an upper surface of the casing 400 as shown in FIG. 1, and detects the user (human body) who approaches the toilet seat 200. A transmission window 310 is provided on a rear part of the toilet lid 300. Therefore, the human body detection sensor 403 can detect existence of the user through the transmission window 310 in the closed state of the toilet lid 300. The controller 405, for example, responses to detection of the human body by the human body detection sensor 403 to open the toilet lid 300 automatically.

The casing 400 may be appropriately provided with various mechanisms such as "warm air drying function" blowing warm air toward "the bottom" of the user seating on the toilet seat 200 to dry, "deodorizing unit", and "indoor warming unit" or the like. At this time, an exhaust port 407 from the deodorizing unit and an outlet port 408 from the indoor warming unit are appropriately provided on a side face of the casing unit. However, in the invention, sanitary washing function and other additional function parts are not always needed to be provided.

Figures 3A, 3B:
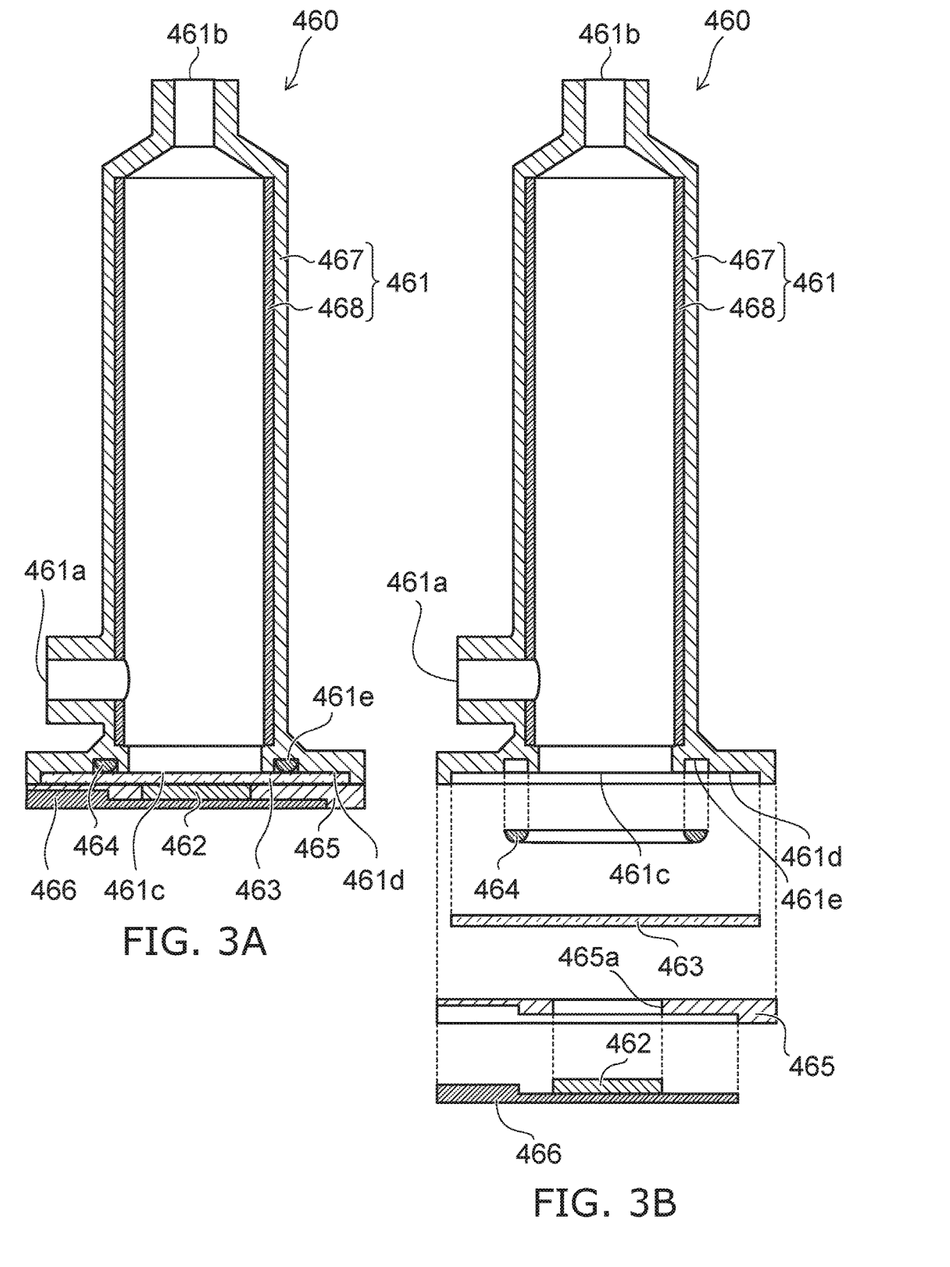
FIG. 3A and FIG. 3B are a cross-sectional view and a resolved cross-sectional view showing schematically an ultraviolet irradiation part according to the embodiment.

FIG. 3A and FIG. 3B are a cross-sectional view and a resolved cross-sectional view showing schematically an ultraviolet irradiation part according to the embodiment.

As shown in FIG. 3A and FIG. 3B, the ultraviolet irradiation part 460 includes the flow channel 461, and a light emitting element 462 (light emitting part). The flow channel 461, for example, allows water to flow inside, which is sent from the pressure modulation device 454, and sends to the flow rate adjustment part 471. The light emitting element 462 irradiates ultraviolet rays to the water flowing in the flow channel. A wavelength of the ultraviolet rays irradiated by the light emitting element 462 is, for example, not less than 200 nm and not more than 400 nm. It is preferably not more than 250 nm. Thereby, the bacteria contained in the water flowing in the flow channel 461 can be adequately reduced. The light emitting element 462 is, for example, LED (Light Emitting Diode). The light emitting element 462 is not limited to LED, but for example, may be LD (Laser Diode) or OLED (Organic Light Emitting Diode) or the like.

The flow channel 461 is straight tubular. An opening 461a is provided on one end of the flow channel 461. An opening 461b is provided on the other end of the flow channel 461. The flow channel 461 allows water to flow between the opening 461a and the opening 461b. The opening 461a is, for example, connected to the pressure modulation device 454. The opening 461b is, for example, connected to the flow rate adjustment part 471. Thereby, the water exiting the pressure modulation part 454 enters the flow channel 461 from the opening 461a, and exits to the flow rate adjustment part 471 through the opening 461b. That is, the flow channel 461 forms a portion of the pipe line 20a. In the flow channel 461, the water flows toward the opening 461b from the opening 461a. To the contrary, the water may be flown from the opening 461b toward the opening 461a.

The opening 461b directs in the same direction as the extending direction of the flow channel 461. On the other hand, the opening 461a directs in a direction orthogonal to the extending direction of the flow channel 461. That is, in this example, the flow channel 461 is a generally L-shaped pipe line. The shape of the flow channel 461 is not limited to this, and may be an arbitrary shape allowing the water to flow inside.

An opening 461c is further provided on one end of the flow rate 461 provided with the opening 461a. The opening 461c directs in the same direction as the extending direction of the flow channel 461. A recessed portion 461d is provided on an outer edge of the opening 461c. An ultraviolet irradiation window 463 is fitted in the recessed portion 461d. The shape of the ultraviolet irradiation window 463 is substantially the same as the shape of the recessed portion 461d. The ultraviolet irradiation window 463 is transmissive to the ultraviolet rays irradiated from the light emitting element 462. The ultraviolet irradiation window 463 causes the ultraviolet rays of the light emitting element 462 disposed on the outside the flow channel 461 to be incident to the inside the flow channel 461. The ultraviolet irradiation window 463 includes, for example, inorganic glass such as quartz glass.

In this way, in this example, the light emitting element 462 is provided outside the flow channel 461. Without limitation to this, for example, at least a portion of the light emitting element 462 may be disposed in the flow channel 461 in the case where the light emitting element 462 is sealed by a package such as a resin or a metal. In this case, the ultraviolet irradiation window 463 may be provided in the package of the light emitting element 462. In this way, the light emitting element 462 (light emitting part) may include the ultraviolet irradiation window 463.

An opening 461e is further provided in the recessed portion 461d. The recessed portion 461e surrounds the outer edge of the opening 461c to be annular. A packing 464 is fitted in the recessed portion 461e. The packing 464 includes an elastic material such as gum. The packing 464 enters into the recessed portion 461e, is sandwiched between the flow channel 461 and the ultraviolet irradiation window 463 to slightly deform elastically, and stops a gap formed between the flow channel 461 and the ultraviolet irradiation window 463. Thereby, the packing 464 suppresses water leakage from the ultraviolet irradiation window 463.

A lid portion 465 is attached to one end of the flow channel 461. The lid portion 465 is attached to the one end of the flow channel 461, and sandwiches the ultraviolet irradiation window 463 and the packing 464 with the flow channel 461. Thereby, the lid portion 465 holds the ultraviolet irradiation window 463 and the packing 464. An opening 465a is provided to the lid portion 465 at a position opposing the ultraviolet irradiation window 463.

The light emitting element 462 is mounted on a substrate 466. The substrate 466 is attached to the lid portion 465 on an opposite side to the flow channel 461. The light emitting element 462 enters the opening 465a of the lid portion 465 in a state where the substrate 466 is attached to the lid portion 465. Thereby, the light emitting element 462 opposes the ultraviolet irradiation window 463, and the ultraviolet rays irradiated from the light emitting element 462 is incident in the flow channel 461 through the ultraviolet irradiation window 463. The light emitting element 462 is, for example, connected to the controller 405 via the substrate 466, and irradiates the ultraviolet rays depending on instruction from the controller 405. Lighting and light-out of the light emitting element 462 are controlled by the controller 405.

In this way, the light emitting element 462 is attached to one end of the flow channel 461 in a straight line. Therefore, the irradiation direction of the ultraviolet rays of the light emitting element 462 is the same as the extending direction of the flow channel 461. For example, an optical axis of the light emitting element 462 is generally the same as the extending direction of the flow channel 461.

The irradiation direction of the ultraviolet rays of the light emitting element 462 is not limited to the above, and may be an arbitrary direction allowing the ultraviolet rays to irradiate the water flowing in the flow channel 461. However, as described above, the irradiation direction of the ultraviolet rays of the light emitting element 462 is set to be the same as the extending direction of the flow channel 461. For example, the direction of the ultraviolet rays irradiated from the light emitting element 462 is set to have a component directing in the same direction as the extending direction of at least of the flow channel 461. Thereby, the ultraviolet rays irradiate the water for a long time, and the bacteria contained in the water can be adequately reduced.

This example shows the flow channel in a straight line, however the shape of the flow rate 461 may be an arbitrary shape allowing the water to flow. A portion in a straight line shape is provided on at least a portion of the flow channel 461, and the extending direction of the portion in a straight line may be set to be the same as the irradiation direction of the ultraviolet rays of the light emitting element 462.

The flow channel 461 includes a main part 467, and a reflection part 468. The reflection part 468 is provided inside the main part 467. The reflection part 468 forms at least a portion of an inner surface of the flow channel 461. The reflection part 468 is reflective to the ultraviolet rays irradiated from the light emitting element 462. A reflectance of the reflection part 468 is higher than a reflectance of the main part 467 to the ultraviolet rays irradiated from the light emitting element 462. The main part 467 includes, for example, a resin material. The reflection part 468 includes, for example, a metal material such as aluminum, stainless steel, silver or the like. The material of the reflection part 468 is not limited to the metal material, but may be, for example, a dielectric multi-layer film or the like. The material of the reflection part 468 is reflective to the ultraviolet rays irradiated from the light emitting element 462, and may be an arbitrary material having a higher reflectance than the main part 467.

Next, the specific example of the operation of the sanitary washing apparatus according to the embodiment will be described with reference to the drawings.

Figure 4:
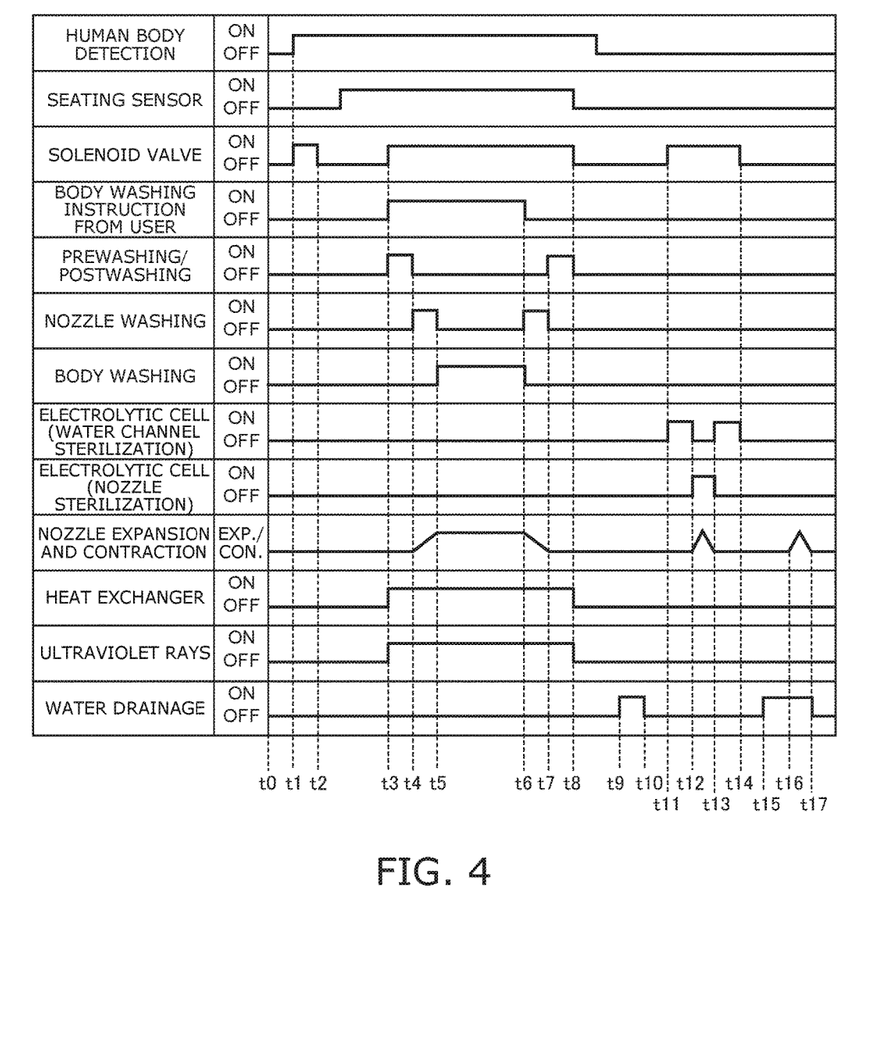
FIG. 4 is a timing chart illustrating a specific example of the operation of the sanitary washing device according to the embodiment.

FIG. 4 is a timing chart illustrating a specific example of the operation of the sanitary washing device according to the embodiment.

As shown in FIG. 4, the nozzle 473 is stored in the casing 400 in a stand-by state before detection of the user by the seating detection sensor 404 (timing t0~t1).

When the human body detection sensor 403 detects the user who enters the toilet room, the controller 405 opens a solenoid valve 431, and sprays clean water onto the surface of the bowl 801 by driving the flow channel switching part 472 so as to cause only the spray nozzle 479 to communicate with the pipe line 20a of the water guide part 20 (timing t1). The time during which the clean water is sprayed is, for example, about 4 seconds (timing t1~t2). In this way, before the user uses the toilet bowl 800, the surface of the bowl 801 is made wet, and thus dirt adhered to the surface of the bowl 801 can be reduced.

When instruction of human body washing is inputted from the operation part 500 in response to the operation by the user, the controller 405 opens the solenoid valve 431, and drives the flow channel switching part 472 so as to cause only both of the bidet washing water discharge port 474a and the bottom washing water discharge port 474b to communicate with the pipe line 20a of the water guide part 20 (timing t3). Thereby, the controller 405 washes the path from the water supply source 10 to the bidet washing water discharge port 474a and the bottom washing water discharge port 474b in a state in which the nozzle 473 is stored.

The controller 405 starts generation of warm water by operating the heat exchange unit 440 at this timing, turns on the light emitting element 462 of the ultraviolet irradiation part 460, and starts irradiation of the ultraviolet rays to the water flowing in the flow channel 461. Thereby, the bacteria contained in the water flowing in the pipe line 20a can be reduced and safe washing water can be supplied to the nozzle 473.

After washing for a prescribed time, the controller 405 drives the flow channel switching part 472 so as to cause only the nozzle washing room 478 to communicate with the pipe line 20a of the water guide part 20, and advances the nozzle 473 into the bowl 801 while performing trunk washing of the nozzle 473 (timing t4).

After advancing the nozzle 473 into the bowl 801, the controller 405 starts the human body washing by driving the flow channel switching part 472 so as to cause at least only one of the bidet washing water discharge port 474a and the bottom washing water discharge port 474b to communicate with the pipe line 20a of the water guide part 20 (timing t5).

When instruction of the human body washing is stopped from the operation part 500, the controller 405 drives the flow channel switching part 472 so as to cause only the nozzle washing room 478 to communicate with the pipe line 20a of the water guide part 20, and stores the nozzle 473 in the casing 400 by driving the nozzle motor 476 (timing t6).

After completing storing the nozzle 473, the controller 405 washes a path from the water supply source 10 to the nozzle 473 by driving the flow channel switching part 472 so as to cause only both of the bidet washing water discharge port 474a and the bottom washing water discharge port 474b to communicate with the pipe line 20a of the water guide part 20 (timing 7).

After washing for a prescribed time, the controller 405 closes the solenoid valve 431, and stops the operations of the heat exchange unit 440 and the ultraviolet irradiation part 460 (timing t8).

After a prescribed time passes from the release of the detection of the user by the human body detection sensor 403, the controller 405 performs water drainage operation of the water collected in the nozzle 473 by driving the flow channel switching part 472 so as to cause each of the bidet washing water discharge port 474a, the washing water discharge port 474b, the nozzle washing room 478, and the spray nozzle 479 to communicate with the pipe line 20a (timing t9). At this time, if the water in the vacuum breaker 452 is reduced, the suction port of the vacuum breaker 452 opens and air is taken into the pipe line 20a. Thereby, the water drainage of the portion downstream of the vacuum breaker 452 is promoted.

After performing the water drainage for a prescribed time, the controller 405 drives the flow channel switching part 472, and closes communication of each of the bidet washing water discharge port 474a, the washing water discharge port 474b, the nozzle washing room 478, and the spray nozzle 479 with the pipe line 20a (timing t10).

After a further prescribed time passes from the water drainage operation, the controller 405 opens the solenoid valve 431, and drives the flow channel switching part 472 so as to cause only both of the bidet washing water discharge port 474a and the bottom washing water discharge port 474b to communicate with the pipe line 20a of the water guide part 20 (timing t11). The controller 405 operates the electrolytic cell unit 450. Thereby, the controller 405 washes the path from the water supply source 10 to the bidet washing water discharge port 474a and the bottom washing water discharge port 474b in a state in which the nozzle 473 is stored. The controller 405 sterilizes, for example, a path from the electrolytic cell unit 450 and the nozzle 473 with the functional water.

After washing for a prescribed time, the controller 405 drives the flow channel switching part 472 so as to cause only the nozzle washing room 478 to communicate with the pipe line 20a of the water guide part 20, and advances/retracts the nozzle 473 by driving the nozzle motor 476 to wash the trunk of the nozzle 473 with the functional water (timing t11~t12). For example, the trunk of the nozzle 473 is sterilized with the functional water.

After washing the trunk of the nozzle 473, the controller 405 washes the path between the electrolytic cell unit 450 and the nozzle 473 again with the functional water, closes the solenoid valve 431, and stops the operation of the electrolytic cell unit 450 (timing t13~t14).

After sterilizing the nozzle 473, the controller 405 performs the water drainage operation again (timing t15). At this time, the controller 405 drives the nozzle motor 476 to advance/retract the nozzle 473 (timing t16~t17). Thereby, for example, a height difference between the vacuum breaker 452 and the respective water discharge ports 474a, 474b increases, and the drainage of the portion downstream of the vacuum breaker 452 can be performed more certainly.

As described in the above, since the sanitary washing apparatus 100 includes the ultraviolet irradiation part 460 disposed between the vacuum breaker 452 and the nozzle 473, even if bacteria is contained in air taken into the vacuum breaker 452, the bacteria contained in the water can be reduced by the ultraviolet irradiation part 460 disposed on a downstream side of the vacuum breaker 452. Thereby, safer washing water can be supplied.

Since the sanitary washing apparatus 100 includes the ultraviolet irradiation part 460 provided on an upstream side of the flow channel switching part 472, even if the washing water is discharged from any water discharge port of the multiple water discharge ports 474a, 474b, the bacteria can be reduced. Therefore, one ultraviolet irradiation part 460 can correspond to the multiple water discharge ports.

If the ultraviolet irradiation part 460 is intended to be disposed in the portion downstream of the flow channel switching part 472, it becomes difficult to dispose the ultraviolet irradiation part 460, such as disposing in the nozzle 473. Therefore, as described above, by disposing the ultraviolet irradiation part 460 on an upstream side of the flow rate switching part 472, freedom of disposing the ultraviolet irradiation part 460 can be improved. For example, increase in size of the nozzle 473 due to disposing the ultraviolet irradiation part 460 or the like can be suppressed.

The sanitary washing apparatus 100 includes the reflection part 468 provided in the flow channel 461 of the ultraviolet irradiation part 460, it is possible to reflect easily the ultraviolet rays in the flow channel 461. Light absorption on an inner surface of the flow channel 461 can be suppressed. For example, it is possible to make the light reach the details of the flow channel 461 and reduce the bacteria contained in the water effectively.

Since the sanitary washing apparatus 100 sets the irradiation direction of the ultraviolet rays of the light emitting element 462 to be the same as the extending direction of the flow channel 461, it is possible to lengthen the time that the ultraviolet rays are incident on the water, and the bacteria can be reduced more certainly.

Figure 5:
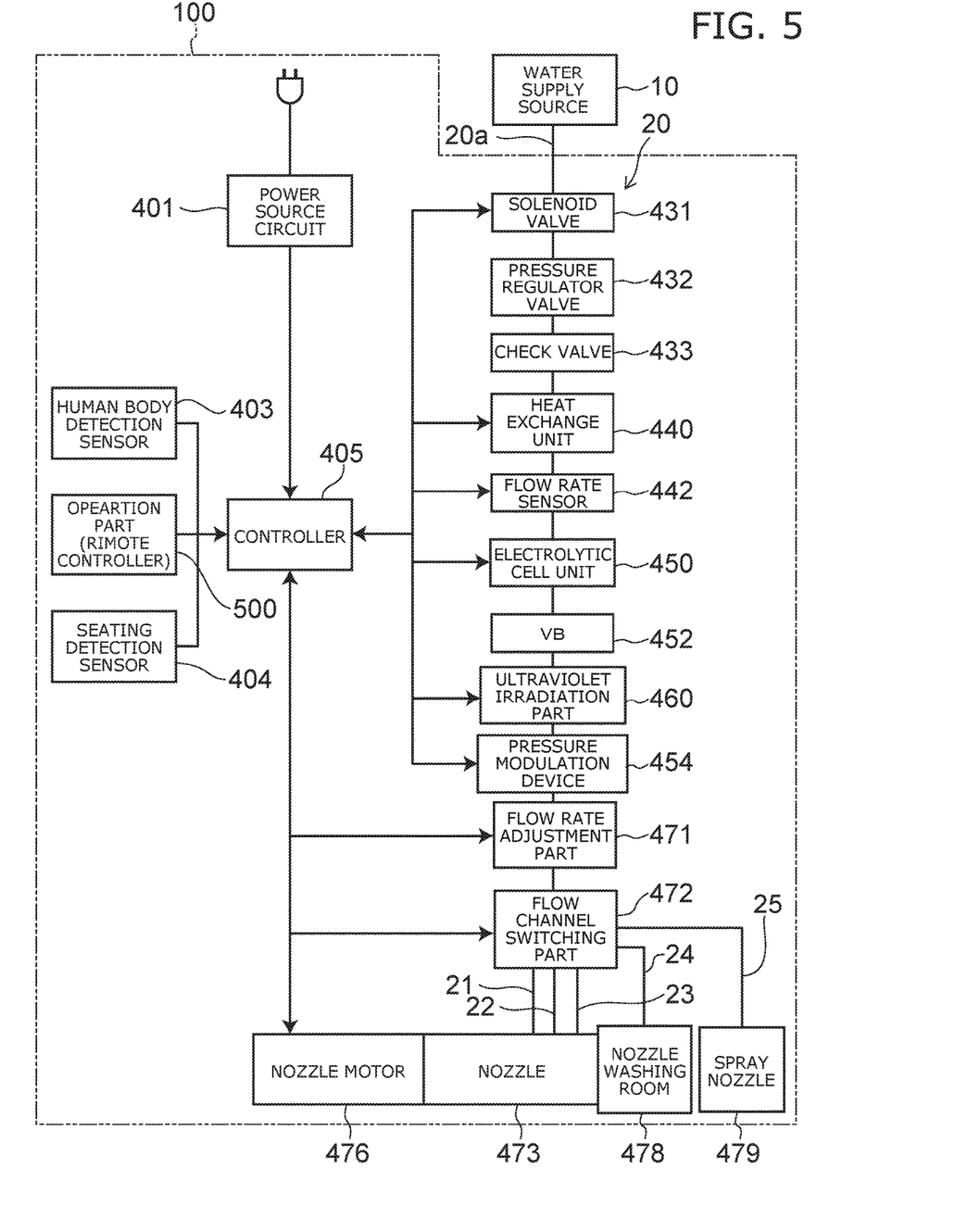
FIG. 5 is a block diagram showing a variation of the sanitary washing device according to the embodiment.

FIG. 5 is a block diagram showing a variation of the sanitary washing device according to the embodiment.

In the embodiment described above, the ultraviolet irradiation part 460 is provided between the pressure modulation device 454 and the flow rate adjustment part 471. Without limitation to this, the ultraviolet irradiation part 460 may be provided between the vacuum breaker 452 and the pressure modulation device 454 as shown in FIG. 5. A disposed position of the ultraviolet irradiation part 460 may be an arbitrary position between the vacuum breaker 452 and the nozzle 473.

In the embodiment described above, the vacuum breaker 452 is provided on a downstream of the electrolytic cell unit 450. The position of the vacuum breaker 452 is not limited to this, and may be an arbitrary position on the path of the water guide part 20. However, it is preferred that the vacuum breaker 452 is disposed on a downstream side as much as possible. Thereby, penetration of dirty water into the sanitary washing apparatus 100 can be adequately suppressed.

Figure 6:
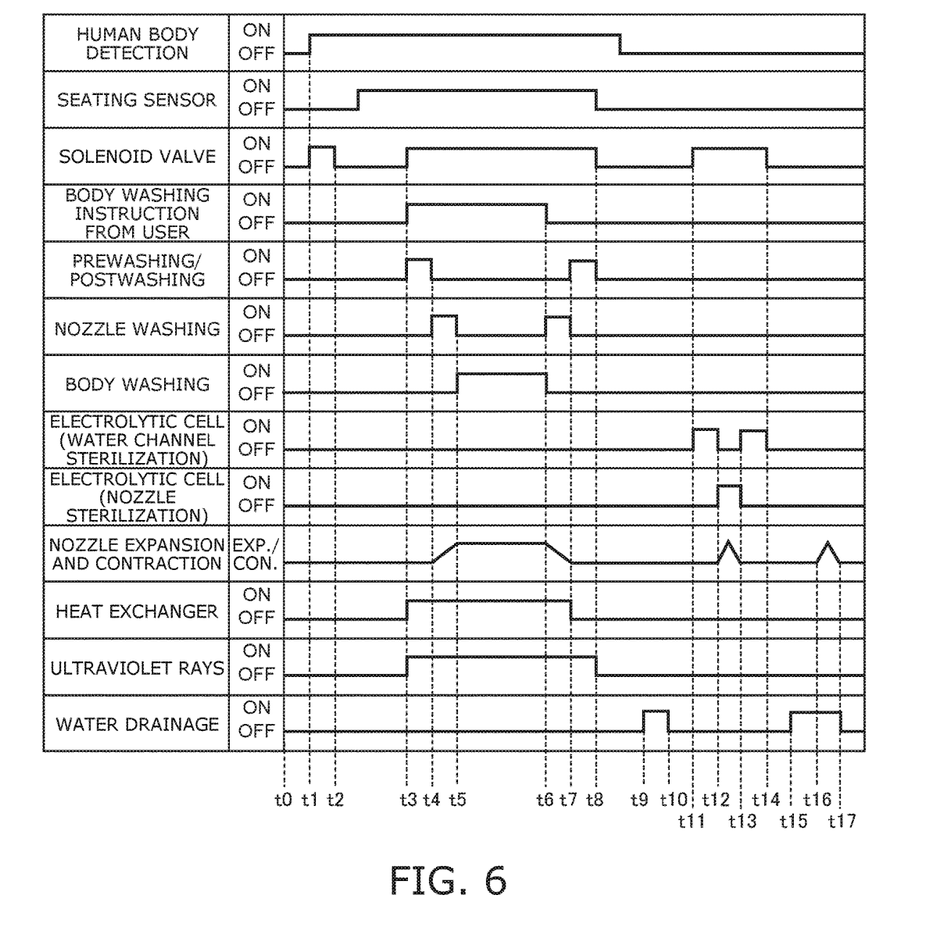
FIG. 6 is a timing chart illustrating the variation of the sanitary washing device according to the embodiment.

FIG. 6 is a timing chart illustrating the variation of the sanitary washing device according to the embodiment.

As shown in FIG. 6, in this example, after the finish of the human body washing, at the timing t7 when washing of the path from the water supply source 10 to the nozzle 473 starts, the operation of the heat exchange unit 440 is stopped. Thereby, for example, energy saving of the sanitary washing apparatus 100 can be made.

When the operation of the heat exchange unit 440 is stopped at the timing t8, the water collected in the water guide part 20 on an upstream side of the vacuum breaker 452 becomes warm water. Thereby, when bacteria are contained in the air taken into the pipe line 20a from the vacuum breaker 452, there is a fear that the bacteria will become easy to breed in the pipe line 20a.

In contrast, when the heat exchange unit 440 is stopped at the timing t7, water collected in the water guide part 20 on the upstream side of the vacuum breaker 452 becomes cold water supplied from the water supply source 10. Thereby, even if bacteria enter the pipe line 20a, the bacteria can be suppressed from breeding.

The timing when the heat exchange unit 440 is stopped may be the timing t6 when the stop of the human body washing is instructed from the operation part 500. In the embodiment described above, while the operation of the ultraviolet irradiation part 460 is stopped at the timing t8, the timing of stopping the operation of the ultraviolet irradiation part 460 is not limited to this, but may be the timing t6, and may be the timing t7.

Figure 7A:
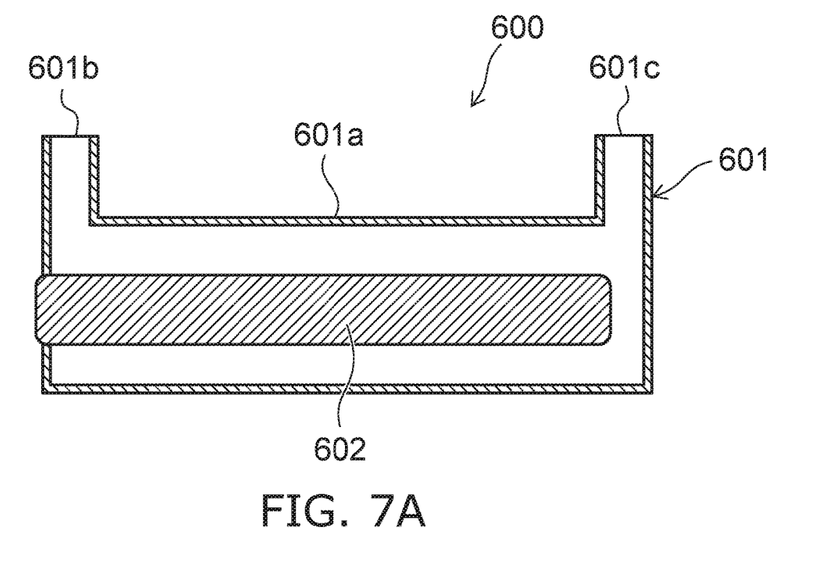
FIG. 7A and FIG. 7B are cross-sectional views showing schematically a variation of the ultraviolet irradiation part according to the embodiment.
Figure 7B:
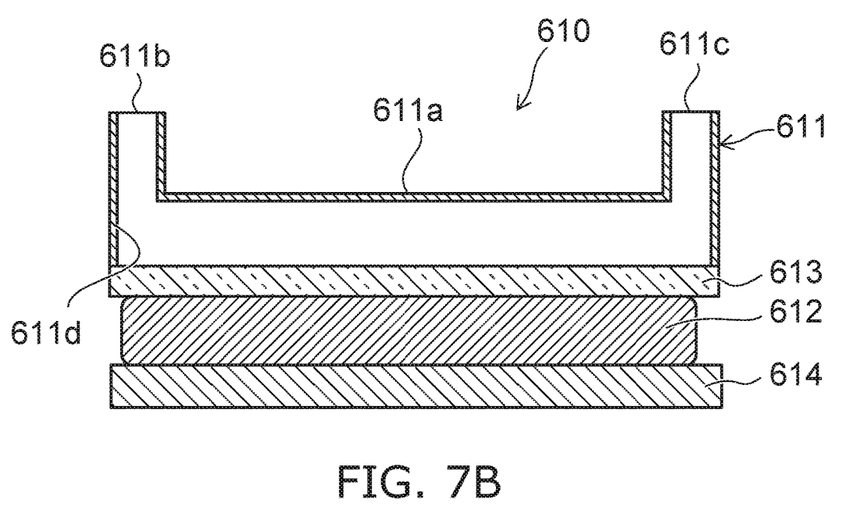

FIG. 7A and FIG. 7B are cross-sectional views showing schematically a variation of the ultraviolet irradiation part according to the embodiment.

As shown in FIG. 7A, an ultraviolet irradiation part 600 includes a flow channel 601 and a cold cathode tube 602 (light emitting part). The flow channel 601 flow water in the interior. The cold cathode tube (CCFL: Cold Cathode Fluorescent lamp) 602 irradiates ultraviolet rays to the water flowing in the flow channel 601. The cold cathode tube 602 extends in one direction and has the one extending direction of the cold cathode tube 602 as a longitudinal direction. The cold cathode tube 602 is, for example, a cylindrical straight tube. The cold cathode tube 602 is inserted in the flow channel 601. The flow channel 601 is formed in a form being along the longitudinal direction of the cold cathode tube 602, that is, the flow channel 601 flows water along the longitudinal direction of the cold cathode tube 602.

The flow channel 601 includes a main part 601a extending in the longitudinal direction of the cold cathode tube 602. The cold cathode tube 602 is inserted in the main part 601a. An opening 601b is provided on one end of the flow channel 601. An opening 601c is provided on the other end of the flow channel 601. The respective openings 601b, 601c direct in a direction generally orthogonal to the extending direction of the main part 601a. That is, in this example, the flow channel 601 is a pipe line having a cross section generally U-shaped. The shape of the flow channel 601 is not limited to this, and may be an arbitrary shape along the longitudinal direction of the cold cathode tube 602.

It is favorable that the flow channel 601 includes, for example, a reflective material such as a metal material to ultraviolet rays irradiated from the cold cathode tube 602. The flow channel 601 may include, for example, a reflective portion and a less reflective portion including a resin material or the like similar to the main part 467 and the reflection part 468 described in the embodiment described above. For example, the flow channel 601 may be reflective to ultraviolet rays by performing a surface treatment such as plating onto a base material including the resin material.

As shown in FIG. 7B, an ultraviolet irradiation part 610 includes a flow channel 611, a cold cathode tube 612, and an ultraviolet irradiation window 613. The cold cathode tube 612 has a straight tube shape as well as the above. The flow channel 611 includes a main part 611a extending in the longitudinal direction and a pair of openings 611b, 611c, and is a pipe line having a cross section generally U-shaped. An opening 611d along the longitudinal direction is provided on the main part 611a of the flow channel 611.

The ultraviolet irradiation window 613 stops the opening 611d of the flow channel 611. The ultraviolet irradiation window 613 is transmissive to the ultraviolet rays irradiated from the cold cathode tube 612. The cold cathode tube 612 opposes to the main part 611a of the flow channel 611 having the ultraviolet irradiation window 613 interposed. Thereby, the cold cathode tube 612 irradiates the ultraviolet rays to the water flowing in the flow channel 611 through the ultraviolet irradiation window 613.

In this way, the cold cathode tube 612 may be provided outside the flow channel 611. In this case, the opening 611d of the flow channel 611 is stopped by the ultraviolet irradiation window 613, and the ultraviolet rays are incident in the flow channel 611 through the ultraviolet irradiation window 613. For example, the opening 611d is stopped by a glass tube of the cold cathode tube 612, and the ultraviolet rays may be incident in the flow channel 611 using the glass tube as the ultraviolet irradiation window. For example, a portion of the flow channel 611 may be used as an irradiation window by forming the flow channel 611 itself from a transmissive material to ultraviolet rays such as quartz glass or the like.

The ultraviolet irradiation part 610 further includes a reflection material 614. The reflection material 614 opposes to the ultraviolet irradiation window 613 having the cold cathode tube 612 interposed. The reflection material 614 is reflective to the ultraviolet rays irradiated from the cold cathode tube 612. The reflection material 614 reflects the ultraviolet rays irradiated from the cold cathode tube 612 toward the opposite side to the flow channel 611, and directs toward the flow channel 611 side. Thereby, utilization efficiency of the ultraviolet rays irradiated from the cold cathode tube 612 can be improved. The reflection material 614 is provided as necessary and is possible to be omitted.

In this way, the light emitting part irradiating the ultraviolet rays to the water flowing in the flow channel is not limited to the light emitting element, and for example, may be a mercury lamp such as a cold cathode tube. The mercury lamp is, for example, a high pressure mercury vapor lamp or a low pressure mercury vapor lamp. The high pressure mercury vapor lamp is, for example, a metal halide lamp or the like. The low pressure mercury vapor lamp is, for example, a cold cathode tube or a hot cathode tube or the like. When using the mercury lamp for the light emitting part, the mercury lamp may be inserted in the flow channel, and may irradiate the ultraviolet rays in the flow channel through the ultraviolet irradiation window. When using the mercury lamp extending in the longitudinal direction, the flow channel is formed in a shape along the longitudinal direction. Thereby, for example, it is possible to lengthen the time that the ultraviolet rays are incident on the water. For example, it is possible that the ultraviolet rays irradiated from the mercury lamp are incident on the water flowing in the flow channel efficiently. Thereby, when using the mercury lamp for the light emitting part, the bacteria can be reduced more certainly.

In the embodiment described above, an integrated type toilet apparatus integrating the sanitary washing device 100 and the toilet bowl 800 is illustrated. The sanitary washing device may be, for example, a so called sheet type toilet seat device which is attached to the toilet bowl detachably.

Hereinabove, the embodiments of the invention are described. However, the invention is not limited to the descriptions. Design modification appropriately made by a person skilled in the art in regard to the embodiments described above is within the scope of the invention to the extent that the features of the invention are included. For example, the shape, the dimension, the material, the disposition, the placement configuration or the like of the components included in the sanitary washing device 100 or the like are not limited to illustrations and can be changed appropriately.

Further, any two or more components of the embodiments may be combined within the extent of technical feasibility and are included in the scope of the invention to the extent that the purport of the invention is included.

According to an aspect of the invention, a sanitary washing device capable of supplying safe washing water is provided.

What is claimed is:

1. A sanitary washing device comprising:
   a nozzle discharging water toward a human body private part;
   a water guide part including a pipe line reaching from a water supply source to the nozzle, and guiding water supplied from the water supply source to the nozzle;
   a vacuum breaker provided on a path of the water guide part, and taking air into the pipe line when water does not flow in the water guide part; and
   an ultraviolet irradiation part provided between the vacuum breaker and the nozzle on the path of the water guide part, and including a flow channel flowing water and a light emitting part irradiating ultraviolet rays to the water flowing in the flow channel.

2. The sanitary washing device according to claim 1, further comprising:
   a flow channel switching part provided on the path of the water guide part,
   the nozzle including a plurality of water discharge ports,
   the flow channel switching part switching a state of communicating with the pipe line and a state of not communicating with the pipe line with respect to each of the plurality of water discharge ports, and
   the ultraviolet irradiation part being provided between the vacuum breaker and the flow channel switching part.

3. The sanitary washing device according to claim 2, wherein the flow channel includes a main part, and a reflection part provided inside the main part and reflecting the ultraviolet rays, and a reflectance of the reflection part to the ultraviolet rays is higher than a reflectance of the main part.

4. The sanitary washing device according to claim 2, wherein at least a portion of the flow channel has a straight pipe shape, the light emitting part is a light emitting element, and an irradiation direction of the ultraviolet rays of the light emitting element is the same as an extending direction of at least the portion of the flow channel.

5. The sanitary washing device according to claim 2, wherein the light emitting part is a mercury lamp extending in one direction, and the flow channel is formed in a form being along the one direction of the mercury lamp.

6. The sanitary washing device according to claim 1, wherein the flow channel includes a main part, and a reflection part provided inside the main part and reflecting the ultraviolet rays, and a reflectance of the reflection part to the ultraviolet rays is higher than a reflectance of the main part.

7. The sanitary washing device according to claim 1, wherein at least a portion of the flow channel has a straight pipe shape, the light emitting part is a light emitting element, and an irradiation direction of the ultraviolet rays of the light emitting element is the same as an extending direction of at least the portion of the flow channel.

8. The sanitary washing device according to claim 1, wherein the light emitting part is a mercury lamp extending in one direction, and the flow channel is formed in a form being along the one direction of the mercury lamp.

9. The sanitary washing device according to claim 1, further comprising:

a solenoid valve being provided on an upstream side from the vacuum breaker on the path of the water guide part, the solenoid valve being configured to open and close the pipe line, the solenoid valve being configured to switch supplying water supplied from the water supply source to the nozzle and stopping water supply to the nozzle; and a controller being configured to control the ultraviolet irradiation part, the controller allowing an operation of the ultraviolet irradiation part in a state that the solenoid valve is opening, and the controller stopping the operation of the ultraviolet irradiation part in a state that the solenoid valve is closing.

10. The sanitary washing device according to claim 1, further comprising:

a casing;

a nozzle motor being configured to move the nozzle between a stored position and an advanced position, the stored position being a position that the nozzle is stored in the casing, the advanced position being a position that the nozzle is advanced ahead from the casing; and a controller being configured to control the ultraviolet irradiation part and the nozzle motor, the controller being configured to perform a prewashing mode and a human body washing mode, the prewashing mode being a mode to flow water to the pipe line in a state that the nozzle is positioned in the stored position, the human body washing mode being a mode to discharge water toward a human body private part from the nozzle in a state that the nozzle is positioned in the advanced position, the controller performing the prewashing mode in response to an instruction of human body washing, performing the human body washing mode after the prewashing mode, and irradiating ultraviolet rays to the water flowing in the flow channel by the ultraviolet irradiation part when the prewashing mode is performed.

* * * * *